(12) United States Patent
Kloetzer et al.

(10) Patent No.: US 8,193,385 B2
(45) Date of Patent: Jun. 5, 2012

(54) METHOD FOR PRODUCING ISOCYANATES

(75) Inventors: Matthias Kloetzer, Kroppen (DE);
Heinrich-Josef Blankertz, Forst (DE);
Gunter Georgi, Lauchhammer (DE);
Eckhard Stroefer, Mannheim (DE);
Volker Krase, Lauchhammer (DE);
Gerhard Schulz, Bad Duerkheim (DE);
Andreas Warzecha,
Lauchhammer-Mitte (DE)

(73) Assignee: BASF SE, Ludwigshafen (DE)

( * ) Notice: Subject to any disclaimer, the term of this patent is extended or adjusted under 35 U.S.C. 154(b) by 486 days.

(21) Appl. No.: 12/438,086

(22) PCT Filed: Aug. 8, 2007

(86) PCT No.: PCT/EP2007/058211
§ 371 (c)(1),
(2), (4) Date: Feb. 19, 2009

(87) PCT Pub. No.: WO2008/025659
PCT Pub. Date: Mar. 6, 2008

(65) Prior Publication Data
US 2009/0275775 A1 Nov. 5, 2009

(30) Foreign Application Priority Data
Aug. 31, 2006 (EP) .................... 06119906

(51) Int. Cl.
*C07C 263/00* (2006.01)
(52) U.S. Cl. ..................... 560/344; 560/345

(58) Field of Classification Search .......... None
See application file for complete search history.

(56) References Cited

U.S. PATENT DOCUMENTS

| 4,497,963 A | 2/1985 | Merger et al. |
| 4,596,678 A | 6/1986 | Merger et al. |
| 5,386,053 A | 1/1995 | Otterbach et al. |
| 5,679,313 A * | 10/1997 | Nojima et al. ............. 423/237 |
| 5,914,428 A | 6/1999 | Yagii et al. |
| 2005/0043562 A1 | 2/2005 | Kohlstruk et al. |

FOREIGN PATENT DOCUMENTS

| DE | 33 14 788 | 10/1984 |
| EP | 0 018 588 | 11/1980 |
| EP | 0 027 952 | 5/1981 |
| EP | 0 028 338 | 5/1981 |
| EP | 0 126 299 | 11/1984 |
| EP | 0 566 925 | 10/1993 |
| EP | 1 512 680 | 3/2005 |

OTHER PUBLICATIONS

U.S. Appl. No. 12/446,460, filed Apr. 21, 2009, Boehling, et al.

* cited by examiner

*Primary Examiner* — Daniel Sullivan
*Assistant Examiner* — Jennifer C Sawyer
(74) *Attorney, Agent, or Firm* — Oblon, Spivak, McClelland, Maier & Neustadt, L.L.P.

(57) ABSTRACT

The invention relates to a multistage process for the continuous preparation of organic, distillable isocyanates, preferably diisocyanates, particularly preferably aliphatic or cycloaliphatic diisocyanates, by reaction of the corresponding organic amines with urea and alcohols to liberate ammonia and form low molecular weight monomeric urethanes and thermal dissociation of the latter, in which by-products formed are at least partly utilized.

7 Claims, No Drawings

METHOD FOR PRODUCING ISOCYANATES

The invention relates to a multistage process for the continuous preparation of organic, distillable isocyanates, preferably diisocyanates, particularly preferably aliphatic or cycloaliphatic diisocyanates, by reaction of the corresponding organic amines with urea and alcohols to liberate ammonia and form low molecular weight monomeric urethanes and thermal dissociation of the latter, in which by-products formed are at least partly utilized.

The industrial processes for preparing organic isocyanates, e.g. aromatic, aliphatic or cycloaliphatic isocyanates, are based on phosgenation of the corresponding organic amines to form carbamoyl chlorides and thermal dissociation of these to form the isocyanates and hydrogen chloride. Apart from the serious environmental protection, disposal and safety problems associated with the use of phosgene, these processes suffer from further critical disadvantages. Thus, the preparation of aliphatic or cycloaliphatic isocyanates proceeds with only quite moderate space-time yields because of the relatively high basicity of the starting amines. A further disadvantage is the formation of undesirable by-products which, even when present in traces, can lead to serious discoloration of the isocyanates. The preparation of hexamethylene 1,6-diisocyanate (HDI) forms, for example, a plurality of by-products of which the most important, viz. 6-chlorohexyl isocyanate, has the additional disadvantage that it can only be separated off from the HDI with a considerable outlay for distillation.

Problems in this type of process are, in particular, the high conversion of chlorine via phosgene and carbamoyl chloride into hydrogen chloride, the toxicity of the phosgene and the corrosivity of the reaction mixture, the lability of the solvents which are generally used and the formation of halogen-comprising residues.

The thermal dissociation of (cyclo)aliphatic and in particular aromatic monourethanes and diurethanes into the corresponding isocyanates and alcohol has been known for a long time and can be carried out either in the gas phase at high temperatures or in the liquid phase at comparatively low temperatures.

In previous decades, there have been many efforts made to eliminate these disadvantages of the process by means of a simpler and improved process. Thus, in the processes for preparing aliphatic and/or cycloaliphatic diurethanes and/or polyurethanes as described in EP 18588 B1 or in EP 28338 B2, primary aliphatic and/or cycloaliphatic diamines and/or polyamines were reacted with O-alkylcarbamic esters in the presence of alcohols at temperatures of from 160 to 300° C. with and without a catalyst. The diurethanes and/or polyurethanes formed can be converted into the corresponding isocyanates. The ammonia formed in the reaction of the amines can be separated off (EP 18588 B1, p. 4, I. 45-46, and p. 5, I. 40-53, EP 28338 B2, p. 6, I. 38-42).

Utilization of the ammonia separated off is not disclosed.

Further publications are concerned with the partial replacement of urea and/or diamines by compounds comprising carbonyl groups, e.g. carbamic esters (e.g. EP 27952 B1 or EP 126299 B1). The phosgene-free process is described in detail in, for example, EP 566925 B1.

The ammonia formed in the reaction of the amines can be separated off (EP 27952 B1, p. 7, I. 44-45, EP 126299 B1, column 5, I. 13-16, EP 566925 B1, column 8, I. 38-47).

Utilization of the ammonia separated off is not disclosed.

EP 1512680 A1 describes a process for preparing cycloaliphatic diisocyanates in which, after reaction of the starting materials to form urethanes, the excess ammonia and alcohol are distilled off together and subsequently separated from one another in a pressure distillation.

Utilization of the ammonia separated off is not disclosed.

The separation operations in the abovementioned documents are restricted to a selective distillation from the reaction mixture.

It was an object of the present invention to prepare distillable organic isocyanates, in particular aliphatic and cycloaliphatic diisocyanates, with high selectivity in improved space-time yields inexpensively and in a simple manner with improved utilization of energy and/or materials.

This object is achieved by a process for preparing isocyanates by reaction of amines with urea and at least one alcohol to form the corresponding urethanes with liberation of ammonia, followed by dissociation of urethanes into the corresponding isocyanates, in which the ammonia liberated is at least partly utilized.

The invention further provides a multistage process for the continuous preparation of organic isocyanates by reaction of the corresponding organic amines with urea and at least one alcohol to form the corresponding urethanes with liberation of ammonia in at least one reactor and thermal dissociation of urethanes, which comprises the following steps and in which a) at least one organic amine is mixed with urea in the presence or preferably in the absence of at least one catalyst and in the absence or preferably in the presence of at least one alcohol,
b) the mixture obtained from a) is reacted in at least one residence reactor to form the corresponding urethane,
c) the ammonia formed is separated off,
d) excess alcohol and further low-boiling secondary components are separated off from the output from c),
e) the urethane which has been freed from the alcohol and low-boiling components in (d) is at least partly fed to a distillation,
f) the urethanes in the distillate from (e) and any proportion of the product from (d) which has not been fed to the distillation (e) is dissociated in a continuous dissociation apparatus into the corresponding isocyanate and alcohol,
g) the crude isocyanate obtained from (f) is purified in at least one distillation and distillation residues obtained are recirculated to the dissociation (f) and/or converted by means of alcohol into urethanes and fed to the reaction unit (a) and/or (b),
h) the reaction product mixture from (f), which comprises a high proportion of urethanes and utilizable compounds, is converted back into urethanes by reaction with alcohols and
i) the ammonia separated off in c) is at least partly utilized thermally.

The process of the invention has improved utilization of materials and/or energy compared to a plain removal of the ammonia, as known from the prior art.

Purely formally, the process of the invention can be schematically represented by the following equation:

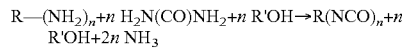

Suitable amines for preparing the monomeric urethanes which can be used according to the invention as intermediates are amines of the formula $R(NH_2)_n$, where R is a polyvalent, preferably divalent organic radical such as an optionally substituted, for example by means of an alkyl group, aromatic or preferably linear or branched, aliphatic or optionally substituted cycloaliphatic radicals.

As suitable aromatic amines, mention may be made by way of example of 2,4- and 2,6-toluenediamine, naphthylenediamine, 4,4'-, 2,4'- and 2,2'-diaminodiphenylmethanes and the corresponding isomer mixtures, 4,4'-, 2,4'- and 2,2'-diaminoditolylmethanes and the corresponding isomer mixtures, benzidine (biphenyl-4,4'-diamine).

Possible aliphatic or cycloaliphatic amines are, for example: 1,4-butanediamine, 2-ethylbutane-1,4-diamine, 1,8-octanediamine, 1,10-decanediamine, 1,12-dodecanediamine, 1,4-cyclohexanediamine, 2-methylcyclohexane-1,3-diamine, 4-methylcyclohexane-1,3-diamine, 1,3- and 1,4-bis (aminomethyl)cyclohexane. Preference is given to using 2-methylpentane-1,5-diamine, 2,2,4- or 2,4,4-trimethylhexane-1,6-diamine, 3 (or 4), 8 (or 9)-bis(aminomethyl)tricyclo [5.2.1.0$^{2,6}$]decane isomer mixtures, 4,4'- or 2,4'-di(aminocyclohexyl)methane, tetramethylxylylenediamine, triaminononane and in particular 1,6-hexanediamine and 3-aminomethyl-3,5,5-trimethylcyclohexylamine.

Suitable alcohols are in principle all cycloaliphatic and preferably aliphatic alcohols. However, preference is given to selecting ones whose boiling points are sufficiently far above the boiling point of the isocyanate, preferably diisocyanate, obtained by means of the thermal dissociation for a virtually quantitative separation of the dissociation products isocyanate, preferably diisocyanate, and alcohol to be possible.

For these reasons, preference is therefore given to using alcohols such as methanol, ethanol, n-propanol, n-butanol, isobutanol, n-pentanol, isopentanol, n-hexanol, isohexanols, cyclopentanol, cyclohexanol, 2-ethylhexanol, decanol or mixtures of the alcohols mentioned, but in particular n-butanol and/or isobutanol.

The individual steps of the process are described below:
a) Mixing of the Reaction Components The mixing of the starting material streams can be carried out in any apparatuses known per se to those skilled in the art. The mixing in step (a) can also be carried out together with the reaction in step (b). Mixing can preferably be carried out in a suitable separate mixing apparatus, particularly preferably in a special mixing apparatus having short mixing times. Separate mixing apparatuses are, for example, mixing circuits, stirred vessels, cascades of stirred vessels, tubes having static mixers or mixing pumps.

It is possible to separate or combine the steps (a) (mixing) and (b) (urethane formation). The urethane formation will usually, depending on the reaction conditions, commence on mixing of the starting materials.

To prepare the urethanes in reaction step (a), the amines are reacted with urea and at least one, preferably precisely one, alcohol in a molar ratio of amine to urea to alcohol of 1:2-20: 5-40 at temperatures of from 50-300° C. and in particular 180-220° C. under a pressure of from 0.1 to 30 bar, preferably from 5-20 bar. Mean reaction times ranging from fractions of a second to minutes are obtained for the process of the invention under these reaction conditions.

To prevent or reduce significant onset of urethane formation during mixing of the components, it is generally sufficient to mix the components at a temperature below 50° C.

The reaction in reaction step (a) can be carried out in the presence of dialkyl carbonates, advantageously in an amount of from 0.1 to 30 mol %, preferably from 1 to 10 mol %, or alkyl carbamates in an amount of advantageously from 1 to 20 mol %, preferably from 5 to 15 mol %, based on the amine, preferably diamine. In particular, mixtures of dialkyl carbonates and alkyl carbamates in the abovementioned ratios are used. As dialkyl carbonates and/or carbamic esters, preference is given to using those whose alkyl radicals correspond to the alkyl radical of the alcohol used.

As indicated above, the reaction in reaction step (a) can also be carried out in the presence of catalysts. These are advantageously used in amounts of from 0.001 to 20% by weight, preferably from 0.001 to 5% by weight, in particular from 0.01 to 0.1% by weight, based on the weight of the amine.

Suitable catalysts are inorganic or organic compounds which comprise one or more cations, preferably one cation, of metals of groups IA, IB, IIA, IIB, IIIB, IVA, IVB, VA, VB, VIIB, VIIB, VIIIB of the Periodic Table of the Elements, defined in accordance with Handbook of Chemistry and Physics 14th Edition, published by Chemical Rubber Publishing Co., 23 Superior Ave. N.E., Cleveland, Ohio. Mention may be made by way of example of the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron and cobalt.

The catalyst can further comprise at least one anion, for example halides such as chlorides and bromides, sulfates, phosphates, nitrates, borates, alkoxides, phenoxides, sulfonates, oxides, oxide hydrates, hydroxides, carboxylates, chelates, carbonates and thiocarbamates or dithiocarbamates.

The catalysts can also be used in the form of their hydrates or ammoniates without significant noticeable disadvantages.

As typical catalysts, mention may be made by way of example of the following compounds: lithium methoxide, lithium ethoxide, lithium propoxide, lithium butoxide, sodium methoxide, potassium tert-butoxide, magnesium methoxide, calcium methoxide, tin(II) chloride, tin(IV) chloride, lead acetate, lead phosphate, antimony(III) chloride, antimony(V) chloride, aluminum acetylacetonate, aluminum isobutoxide, aluminum trichloride, bismuth (II) chloride, copper(II) acetate, copper(II) sulfate, copper(II) nitrate, bis (triphenylphosphine oxide)copper(II) chloride, copper molybdate, silver acetate, gold acetate, zinc oxide, zinc chloride, zinc acetate, zinc acetylacetonate, zinc octoate, zinc oxalate, zinc hexoxide, zinc benzoate, zinc undecanoate, cerium(IV) oxide, uranyl acetate, titanium tetrabutoxide, titanium tetrachloride, titanium tetraphenoxide, titanium naphthenate, vanadium(III) chloride, vanadium acetylacetonate, chromium(III) chloride, molybdenum(VI) oxide, molybdenum acetylacetonate, tungsten(VI) oxide, manganese(II) chloride, manganese(II) acetate, manganese(III) acetate, iron (II) acetate, iron(II) acetate, iron phosphate, iron oxalate, iron(III) chloride, iron(II) bromide, cobalt acetate, cobalt chloride, cobalt sulfate, cobalt naphthenate, nickel chloride, nickel acetate and nickel naphthenate and also mixtures thereof.

As preferred catalysts, mention may be made by way of example of the following compounds: lithium butoxide, aluminum acetylacetonate, zinc acetylacetonate, titanium tetrabutoxide and zirconium tetrabutoxide.

In the process of the invention, the mixing of the starting material streams is effected in a suitable special mixing apparatus which has short mixing times.

The mixing time in special mixing apparatuses having a short mixing time is usually from 0.0001 s to 2 s, preferably from 0.0005 to 1 s, particularly preferably from 0.001 to 0.5 s, very particularly preferably from 0.005 to 0.2 s and in particular from 0.007 to 0.1 s. For the purposes of the present invention, the mixing time is the time which elapses from commencement of the mixing process until 97.5% of the fluid elements of the mixture obtained have a mixing fraction which, based on the theoretical final value of the mixing fraction of the mixture obtained on reaching a state of perfect mixing, differs by less than 2.5% from this final value of the mixing fraction (for the concept of the mixing fraction, see, for example, J. Warnatz, U. Maas, R. W. Dibble: Verbrennung, Springer Verlag, Berlin Heidelberg New York, 1997, 2nd edition, p. 134.). As mixing apparatus, preference is given to using a mixing circuit, a stirred vessel, a mixing pump or a nozzle mixing apparatus, for example coaxial mixing nozzles, Y- or T-mixers or a vortex impinging jet mixing configuration, preferably a mixing circuit, a stirred vessel, a mixing pump or a nozzle mixing apparatus.

When a mixing circuit or a stirred vessel is used as mixing apparatus, it is important that the amine solution is sprayed in at a high velocity. The velocities are usually in the range from 10 to 100 m/s, preferably from 20 to 80 m/s. Preference is given to using a mixing nozzle and a mixing pump as mixing apparatus. Particular preference is given to using a mixing nozzle as mixing apparatus. Here, it is important that both the alcohol stream and the amine stream are introduced at a high velocity into the mixing nozzle. The velocities are in the range from 10 to 100 m/s, preferably from 20 to 80 m/s.

Here, the pressure in the feed lines to the nozzle is considerably higher than in the outlet of the mixing nozzle, but usually not greater than 110 bar abs, preferably not greater than 100 bar abs, particularly preferably in the range from 5 to 95 bar abs, very particularly preferably from 10 to 50 bar abs and in particular from 10 to 30 bar abs.

The pressure at the outlet from the mixing apparatus is general above the reaction pressure in step b), for example in the range from 5 to 100 bar, preferably from 10 to 80 bar, particularly preferably from 10 to 50 bar.

The temperature of the output from the mixing apparatus is generally from 25 to 240° C., preferably 30-190° C. and particularly preferably 40-180° C.

The output from the mixing apparatus can be brought to the temperature desired in step b) by means of a heat exchanger before it is introduced into that step.

The conversion based on amino groups in the amine used to urethane groups in step a) is generally not more than 10%, preferably not more than 5%, particularly preferably not more than 2%.

The transfer of the reaction product mixture from step a) into the subsequent step can advantageously be carried out via pressure regulating valves, with the pressure at the outlet from step a) being at least 1 bar, preferably at least 2 bar, particularly preferably at least 3 bar, above the pressure prevailing in step b).

b) Reaction of the Mixture from a)

The liquid phase leaving the mixing apparatus is fed to at least one, preferably precisely one, reactor operated with two phases (gas/liquid). This can be a reactor with no backmixing, for example a stirred vessel, or preferably a reactor which has no backmixing or a little backmixing, for example tube reactors or cascades of stirred vessels. The mixture is preferably fed to a tube reactor or a plurality of reactors whose residence time distribution resembles that of a tube reactor in which the gas phase is conveyed in cocurrent with the liquid phase.

The tube reactor should preferably be at least largely free of backmixing. This is achieved, for example, by means of the ratio of the diameter of the tube reactor to its length or by internals such as perforated plates, slotted plates or static mixers. The freedom from backmixing is preferably achieved by means of the ratio of length to diameter of the tube reactor.

Suitable tube reactors are, for example, tubes whose length to diameter ratio is greater than 5, preferably greater than 6, particularly preferably greater than 10.

The Bodenstein number of the tube reactor should be greater than 5, preferably greater than 6, particularly preferably greater than 10, very particularly preferably from 10 to 600 and in particular from 10 to 100.

An aspect which contributes significantly to the invention is the presence of a flow regime which is ideally plug flow and in reality should approximate this to the extent necessary. For this purpose, axial mixing, i.e. mixing along the flow direction through the reactor, is reduced greatly and the flow is ideally turbulent.

This is achieved in practice by means of high flow velocities and low cross-sectional areas, for example in flow tubes.

The tube reactor can have any orientation in space. It is preferably constructed as a vertical tube reactor through which flow particularly preferably occurs from the bottom upward.

The tube reactor can be isothermal or preferably heated. Heating can be effected by means of walled heating or by means of internal tubes or plates. Heating is preferably effected through the wall.

Of course, the tube reactor can also comprise a plurality of tubular pieces connected in series, as long as freedom from backmixing continues to be ensured. If necessary, phase separators for separating liquid and gaseous phases can optionally be provided along the tube reactor, for example between such tubular pieces, so that ammonia formed during the reaction can be separated off and the equilibrium of the reaction is shifted.

To increase the production capacity, it is also possible according to the invention for a plurality of tube reactors to be connected in parallel.

If appropriate, it is possible, as indicated above, for further urea and/or alcohol or preferably amine to be introduced into the tube reactor at one or more points, for example at the beginning and in the middle of the tube reactor.

The mean residence time in the tube reactor is generally from 10 seconds to 5 hours, preferably from 20 seconds to 20 minutes, particularly preferably from 30 seconds to 10 minutes.

To keep the amount of gas going to the next step small, the output from the tube reactor can, in a preferred embodiment, be fed into a phase separator and the liquid phase taken off from the phase separator can then be fed to the next step.

Such a phase separator is a vessel in which phase separation of gas phase and liquid phase is achieved by calming of the two-phase stream leaving the cocurrent reactor.

The phase separator can be isothermal or preferably heated in order to prevent the precipitation of sparingly soluble by-products. Heating can, for example, be effected via the wall or via a circuit having an external heat exchanger. When an external heat ex-changer is used, normal insulation of the heat exchanger suffices.

The temperature in the tube reactor and in any phase separator present is generally from 50° C. to 300° C., preferably from 180° C. to 220° C.

The pressure in step b) is generally from 0.1 bar abs to 30 bar abs and preferably from 5 to 20 bar abs.

The transfer of the reaction product mixture from step b) to the next step can advantageously take place via pressure regulating valves, with the pressure in step b) generally being at least 0.1 bar above the pressure prevailing in step c). If this is not the case, the transfer can be effected, for example, by means of a pump or barometrically.

The residence time in step b) is selected so that the conversion, based on amino groups in the amine used into urethane groups, after leaving the (tube) reactor is at least 95%, preferably at least 98%, particularly preferably at least 99%, very particularly preferably at least 99.5% and especially at least 99.8%. Reaction conditions which lead to complete conversion are desirable.

The total residence time in steps a) and b) together is usually less than 5 hours, preferably less than 4 hours and particularly preferably less than 3 hours.

The reaction mixture resulting from (b) can in the case of complete conversion of the amine groups to the urethane be fed directly to the ammonia removal (c) or it is fed to a further reactor or reactor system to achieve complete conversion. As reactors, it is possible to use further tube reactors, cascades of mixing reactors or columns having the necessary mean residence time.

If the conversion, based on amino groups in the amine used into urethane groups, after leaving the tube reactor is not yet complete and is, for example, less than 95%, the output can be subjected to an after-reaction.

For this purpose, the reaction mixture can, to complete the conversion, be left to react in a further tube reactor or else in a backmixed reactor, preferably until the conversion is 98% or more.

Here, a backmixed reactor system is one whose Bodenstein number is less than 5, preferably less than 4.

c) Ammonia Removal

Columns are advantageously used for separating off the ammonia; the ammonia is preferably separated off by distillation. This gives good separation between the alcohol and ammonia. The removal is usually carried out in a pressure range of 0.01-20 bar, preferably 0.04-15 bar. The necessary temperatures depend on the alcohol used or the alcohol mixture. In the case of n-butanol, the temperature is, for example, 60-150° C., preferably from 80 to 140° C.

It has been found to be advantageous for the ammonia formed to be separated off from the reaction mixture immediately, so that coating by ammonium carbamate, which is formed in minimal amounts from ammonia and carbon dioxide from decomposition of urea, can be avoided.

This distillation unit is of a construction known per se and has the usual internals. Possible column internals are in principle all customary internals, for example trays, ordered packing and/or beds of random packing elements. Among trays, bubble cap trays, sieve trays, valve trays, Thormann trays and/or dual-flow trays are preferred; among beds of random packing elements, those comprising rings, helices, saddle bodies, Raschig, Intos or Pall rings, barrel or Intalox saddles, Top-Pak, etc., or braids are preferred. Preference is given to using ordered packing.

The distillation column preferably has 10-20 theoretical plates.

The removal by distillation can be aided by a gas which is inert under the reaction conditions (stripping gas). Such stripping gases are, for example, ones having an oxygen content of less than 2% by volume, preferably less than 1% by volume, particularly preferably less than 0.5% by volume; preference is given to nitrogen, argon, helium, nitrogen/noble gas mixtures, particularly preferably nitrogen.

The mixture taken off as vapor comprises ammonia as main constituent, for example in a proportion of more than 50% by weight, preferably more than 65% by weight, particularly preferably more than 75% by weight, very particularly preferably more than 85% by weight and in particular more than 90% by weight. Further constituents of the vapor stream are the alcohol used, the ether formed from this, the dialkyl carbonate or carbamates formed from the alcohol and also further gaseous constituents such as carbon dioxide, nitrogen and oxygen. This stream can then, as described below for step (i), be utilized, preferably burnt.

d) Removal of the Excess Alcohol

Alcohol, dialkyl carbonates (if they have been formed or are present in the reaction mixture) or alkyl carbamates or mixtures of at least two of these components are then separated off from the resulting ammonia-depleted reaction mixture and are preferably recirculated to reaction step (a) and/or (b).

To separate off the components, the reaction mixture is advantageously depressurized from the pressure level of reaction step (b) to a pressure in the range from 1 to 500 mbar, preferably from 10 to 100 mbar. This gives gaseous vapors ($d_L$) which comprise predominantly alcohol together with from 0 to 30% by weight, preferably from 1 to 10% by weight, of dialkyl carbonate and/or from 1 to 50% by weight, preferably from 1 to 20% by weight, of alkyl carbamates and a liquid output which consists essentially of the monomeric urethane, preferably diurethane, and possibly oligoureapolyurethanes and high-boiling oligomers.

The vapors obtained ($d_L$) are separated in subsequent purification stages, advantageously distillation stages, preferably by rectification, and the products of value alcohol and alkyl carbamates isolated here are recirculated individually or as a mixture to, preferably, reaction step (a) for formation of the monomeric urethanes.

This distillation unit is of a construction known per se and has the usual internals. Possible column internals are in principle all customary internals, for example trays, ordered packing and/or beds of random packing elements. Among trays, bubble cap trays, sieve trays, valve trays, Thormann trays and/or dual-flow trays are preferred; among beds of random packing elements, those comprising rings, helices, saddle bodies, Raschig, Intos or Pall rings, barrel or Intalox saddles, Top-Pak, etc., or braids are preferred. Preference is given to using ordered packing.

The distillation column preferably has 10-20 theoretical plates.

The removal of the alcohol or the alcohol mixture by distillation is preferably carried out using a flash apparatus. This apparatus can be a vessel or a combination of vessel and column, preferably a column, with the alcohol or alcohol mixture being able to be taken off at the top and the urethane being able to be taken off at the bottom. The fraction taken off at the top of the column can comprise further substances having a boiling point lower than that of urethane in addition to the alcohol. The separation is carried out in a pressure range from 0.001 to 2 bar, preferably 0.02-0.5 bar.

In a preferred embodiment of the present invention, very complete separation of ammonia and alcohol as described above under c) is dispensed with. For this purpose, steps c) and d) are combined into one step so that the number of theoretical plates in such a combined step is smaller than the sum of the theoretical plates in steps c) and d).

Here, it is accepted that the vapor stream can comprise not only ammonia but also alcohol and possibly further low boilers, for example up to 5% by weight of dialkyl carbonates or carbamates, which then contribute positively to the energy balance in the thermal utilization (step i)) by combustion. In the separation, the alcohol is obtained in a purity of more than 98% by weight, so that it can readily be reused in the reaction, i.e. in step a) and/or b).

A further advantage is that the separation apparatus in such a combined step can be made simpler than in two separate steps.

e) Urethane Purification

The liquid reaction mixture (d) comprising the monomeric urethanes, preferably diurethanes, and possibly oligoureapolyurethanes and high-boiling oligomers which is generally obtained as bottom output after the vapor has been separated off in reaction step (d) can either be conveyed in its entirety to the next step or is preferably divided into two substreams having a weight ratio of 5-50:95-50, preferably 10-30:90-70.

The equal-sized or preferably smaller substream is fractionally distilled by means of a customary distillation unit, preferably a thin film evaporator, at a temperature of from 170 to 240° C., preferably from 180 to 230° C., and under a pressure of 0.001-1 bar, preferably 0.002-0.01 bar, into a product of value which comprises the urethanes, preferably diurethanes, and the relatively low-boiling by-products ($e_L$) and undistillable by-products ($e_H$) which are separated off from the production process and are usually discarded as a residue which cannot be utilized. This can, in a preferred embodiment, be passed to thermal utilization. The desired product (distillate) is combined with the equal-sized or preferably larger other substream and the combined reaction mixture comprising urethanes, preferably diurethanes, is fed to the thermal dissociation (f).

As a result of this process measure in reaction step (e), the proportion of undistillable by-products in the reaction mixture, which form in the sequential subreactions and would continually accumulate in the reaction circuit due to the recirculation of utilizable starting materials, is limited to a content of from 3 to 30% by weight, preferably from 5 to 20% by weight, and a reaction proceeding in a trouble-free fashion and with high selectivity is thereby ensured.

As distillation apparatuses, it is possible to use thin film evaporators or short path evaporators. The urethane is distilled at pressures of 0.001-1 bar, preferably in the range 0.002-0.01 bar. The distillate ($e_L$) is fed to the dissociation (f).

The bottoms comprising high boilers ($e_H$) are preferably discarded or, less preferably, can be partly passed onto the reurethanization (h). The bottoms comprising high boilers ($e_H$) can, in a preferred embodiment, be passed to the thermal utilization.

f) Urethane Dissociation

The reaction mixture comprising urethanes, preferably diurethanes, obtained in reaction step (e) is continuously thermally dissociated in a suitable apparatus, preferably in the absence of solvents in the liquid phase in the presence of catalysts at temperatures of from 200 to 300° C., preferably from 220 to 280° C., and under a reduced pressure of 0.01-0.6 bar, preferably in the range 0.02-0.1 bar. The conversion of urethane into isocyanate, preferably diurethane into diisocyanate, in the thermal dissociation apparatus can be chosen largely freely as a function of the urethane used and is advantageously in the range from 10 to 98% by weight, preferably from 40 to 90% by weight, of the amount of urethane fed in.

The undissociated part of the reaction mixture, which comprises unreacted urethanes, oligourea-polyurethanes, high-boiling oligomers and other reutilizable and unutilizable by-products, is separated off, continuously discharged from the dissociation apparatus ($f_H$) and recirculated either directly or, if appropriate, after reaction with alcohol in the reurethanization (h) to the reaction step (a) and/or (b).

Catalysts used for the chemical dissociation of urethanes are, for example, the above-mentioned inorganic and organic compounds which catalyze urethane formation.

Catalysts which have been found to be particularly useful and are therefore preferably used are dibutyltin dilaurate, iron (III) acetylacetonate, cobalt (II) acetylacetonate, zinc acetylacetonate, zirconium tetra-n-butoxide and tin (II) dioctoate.

Suitable dissociation apparatuses are, for example, cylindrical dissociation reactors such as tube ovens or preferably evaporators, for example thin film evaporators or bulk evaporators, e.g. Robert evaporators, Herbert evaporators, Caddie-type evaporators, plate crackers and preferably heating plug evaporators.

The separation of the dissociation products is effected in a column in which the isocyanate is usually taken off at the side ($f_M$) and the alcohol ($f_L$) is usually taken off at the top.

g) Isocyanate Purification

The crude isocyanate mixture is freed of recombination products, by-products and any solvent present in a subsequent distillation. The by-products are preferably recirculated to the thermal dissociation. Part can also be discharged.

The dissociation products formed in the thermal dissociation, which are composed first and foremost of alcohol, isocyanate, preferably diisocyanate, and partially dissociated urethanes, are then advantageously separated by means of one or more distillation columns, preferably by rectification at temperatures of from 100 to 220° C., preferably from 120 to 170° C., and a pressure of from 1 to 200 mbar, preferably from 5 to 50 mbar, into low boilers and in particular alcohol ($g_L$) and a crude isocyanate mixture ($g_M$) having an isocyanate content of from 85 to 99% by weight, preferably from 95 to 99% by weight. The relatively high-boiling by-products ($g_H$) obtained in the separation by distillation and in particular the undissociated and partially dissociated urethanes are preferably fed into the dissociation apparatus (f) and/or reurethanization (h).

Here, the index "L" denotes low-boiling streams of the individual steps, the index "H" denotes high-boiling streams and "M" denotes middle-boiling streams.

The crude isocyanate mixture ($g_M$) which is preferably obtained by rectification is purified by distillation at a temperature of from 100 to 180° C. and under a pressure of from 1 to 50 mbar, with the individual fractions being recirculated or isolated as pure product. As indicated above, the overhead fraction obtained in the purifying distillation preferably employed, which preferably comprises isocyanate, in particular diisocyanate, is, if appropriate after reaction of the free isocyanate groups with alcohol, recirculated to reaction step (a) and/or (b), the side fraction which comprises pure isocyanate, in particular diisocyanate, preferably in a purity of at least 98% by weight, in particular above 99% by weight, is taken off and conveyed to storage and the bottom fraction which comprises the partially dissociated urethanes and isocyanates as significant components is preferably recirculated to the dissociation apparatus for thermal dissociation.

However, in other process variants, the bottom fraction ($g_H$) can also be recirculated to the distillation column (d) for the separation of crude isocyanate and alcohol or to reaction step (a) and/or (b), viz. urethane formation. It is also possible for the bottom fraction to be divided into 2 or 3 product streams which are preferably recirculated to the urethane formation (a) and/or the dissociation apparatus (f) and, if appropriate, to the distillation column (g) and/or to the reurethanization (h).

h) Reurethanization

The reaction output ($f_H$) from f) and/or distillation residues ($g_H$) from (g) are preferably fed back into the process. Here, the isocyanate groups and/or allophanates and/or ureas or other reactive constituents comprised in this mixture are converted by means of alcohol into urethanes. It is possible for these reactions to be carried out in separate reactors such as mixing reactors or flow tubes or in (b).

Temperatures of 100-250° C., preferably 150-220° C., are required for the reaction of the residues with alcohol. The mean residence times here are in the range from a few minutes to some hours. In general, the reaction is preferably carried out in a single liquid phase. The pressure during the reaction plays no particular role except that it should be sufficient to keep the reaction mixture liquid.

For this purpose, it is possible, for example, to combine the streams ($f_H$) and/or ($g_H$) and, if appropriate, part of the stream ($e_H$) with alcohol in such amounts that the molar ratio of NCO groups or their equivalents, i.e., for example, urethane groups, to hydroxy groups from the alcohol is up to 1:100, preferably up to 1:20, particularly preferably up to 1:10.

The alcohol can, for example, be the low-boiling stream ($d_L$) from step (d) and/or the alcohol-comprising stream ($f_L$) from the urethane dissociation (f) and/or fresh alcohol.

If a catalyst is to be used, it is preferably the same catalyst as in the urethane formation step (b).

For the reurethanization, the reaction mixture is reacted in the presence or absence of catalysts for a period of from 1 to 150 minutes, preferably from 3 to 60 minutes, at a temperature of from 20 to 200° C., preferably from 50 to 170° C., and a pressure of from 0.5 to 20 bar, preferably from 1 to 15 bar.

The reaction can be carried out in a continuous cascade of vessels or in a tube reactor.

As catalysts, it is in principle possible to use all compounds which promote the reaction of NCO groups with OH groups or the cleavage (alcoholysis) of high molecular weight compounds. Examples which may be mentioned are tin octoate, dibutyltin dilaurate, tin chloride, zinc dichloride, tin (II) dioctoate and triethylamine.

(i) Utilization

According to the invention, the ammonia separated off in step c) or the combined step made up of steps c) and d) is at least partly utilized, preferably utilized thermally.

A possible method of nonthermal utilization is to feed the ammonia which has been separated off to a plant for producing downstream products of ammonia, preferably the preparation of urea or melamine by processes known per se. If the ammonia is fed to the preparation of urea, the materials circuit of the process of the invention is closed, since the urea prepared in this way can be fed back into a process for preparing isocyanates, for example by the process of the invention.

It is an advantage here for the content of organic material comprised in the ammonia which has been separated off to be separated off beforehand in order to avoid secondary reactions in the next step. This is preferably effected by absorption on a suitable material, for example activated carbon, aluminum oxide, silica gel or titanium dioxide. After loading, this material can be regenerated, for example by desorption or flaming.

However, preference is given to thermal utilization of the ammonia which has been separated off, in which ammonia is burnt together with oxygen or an oxygen-comprising gas, preferably air.

Possible reactions here are the reactions known to those skilled in the art for the combustion of ammonia, preferably the reaction (i1)

$$4\,NH_3 + 5\,O_2 \rightarrow 4\,NO + 6\,H_2O$$

as first step of the Ostwald process for preparing nitric acid. This reaction is generally followed by the further oxidation according to $$2\,NO + O_2 \rightarrow 2\,NO_2 \rightleftharpoons N_2O_4$$

and absorption of the resulting nitrogen dioxide in water, resulting in liberation of nitrogen monoxide.

According to the invention, the form in which the Ostwald process is carried out is not critical.

If the ammonia is oxidized to nitrogen oxides according to equation (i1), preference is given, according to the invention, to no further residues from the process for preparing the isocyanates, for example the stream ($e_H$) or ($f_H$), being introduced into the combustion.

The Ostwald process can, for example, be carried out as a monopressure process in which ammonia combustion and $NO_x$ absorption are carried out in essentially the same pressure range. This can be intermediate pressure (230-600 kPa) or high pressure (700-1100 kPa).

The process can also be performed as a dual-pressure process. Here, the combustion is generally carried out at 400-600 kPa and the absorption is carried out at 900-1400 kPa.

The temperatures for the oxidation are generally in the range from 700 to 1000° C., preferably from 800 to 900° C. and particularly preferably from 830 to 850° C.

The ammonia/air mixture fed to ammonia combustion should have an ammonia content of not more than 11% (in the case of combustion under high pressure) or not more than 13.5% (in the case of combustion under intermediate pressure).

As catalysts, use is made of catalysts known per se. These are preferably noble metals, particularly preferably platinum catalysts which can, if appropriate, be alloyed with 5-10% of rhodium and/or 5% of palladium.

The catalysts are usually used in the form of meshes, gauzes, braids or wires or shaped bodies produced therefrom, or as supports, for example ceramic grids, coated with noble metal.

The wires used for producing the gauzes generally have a diameter of 0.06-0.076 mm. The gauzes are very fine and can have from 500 to 2000 openings/cm², preferably from 800 to 1500 and particularly preferably about 1000 openings/cm².

However, particular preference is given to reaction (i2)

$$4\,NH_3 + 3\,O_2 \rightarrow 2\,N_2 + 6\,H_2O$$

in which ammonia is burnt to form molecular nitrogen ($N_2$).

If appropriate, this reaction can be combined with the comproportionation with nitrogen monoxide (i3)

$$4\,NH_3 + 6\,NO \rightarrow 5\,N_2 + 6\,H_2O$$

to form molecular nitrogen.

As an alternative, a decomposition of ammonia according to (i4) is also conceivable:

$$2\,NH_3 \rightarrow N_2 + 3\,H_2$$

The reactions (i1) to (i3) are exothermic (i1: −904 kJ/mol, i2: −1268 kJ/mol, i3: −1808 kJ/mol), so that the energy released in these reactions can, according to the invention, preferably be introduced into the process for preparing the isocyanates, for example for generating steam for the vaporizers of distillations or particularly preferably for the dissociation (f).

The ammonia in the offgas can preferably be burnt according to reaction (i3). This can, as is known from the prior art, be carried out as described in, for example, K. Stein-brunner, R. Becker, H. Seifert, "Verbrennung $NH_3$-haltiger Prozeβgase", Chem.-Ing.-Tech. 67 (1995) No. 2, 199-202.

This generally requires high temperatures of 800° C. and above, at which part of the ammonia is converted into nitrogen oxides. Apart from a residual content of a few per-cent of ammonia, part of the ammonia is oxidized further to nitrogen oxides ($NO_x$) which in turn are environmental pollutants.

For the present purposes, nitrogen oxides ($NO_x$) are compounds of any stoichiometry which consist exclusively of nitrogen and oxygen, e.g. $N_4O$, $N_2O$, $NO$, $N_2O_3$, $NO_2$, $N_2O_5$ and $NO_3$ (as per Römpp-Online, keyword: Stickstoffoxide, document RD-19-04121, Mar. 2002).

The reaction can be carried out over catalysts over which ammonia is oxidized to nitrogen in the presence of an excess of oxygen (see: EP 686423 A2, EP 706816 A1).

These can be, for example, catalysts which comprise silver, beryllium, magnesium, zinc or aluminum in the form of the metals or titanium, vanadium, iron, tungsten, nickel, cobalt, copper, chromium, uranium, molybdenum or tin or mixtures thereof in the form of their oxides and/or sulfides, preferably copper, cobalt, iron, chromium, nickel, vanadium or manganese or mixtures thereof in the form of their oxides.

Suitable supports are aluminum oxide, silicon dioxide and titanium dioxide in the form of any shaped bodies, for example rings, extrudates or pellets for all-active catalysts or honeycomb structures for coated catalysts.

Catalysts based on platinum are particularly useful.

The thermal combustion of ammonia forms predominantly nitrogen, but nitrogen oxides ($NO_x$) are also formed.

This occurs firstly via the reaction (i1) but also as a result of the reactions $$4\ NH_3 + 7\ O_2 \rightarrow 4\ NO_2 + 6\ H_2O$$

and/or $$2\ NH_3 + 2\ O_2 \rightarrow N_2O + 3\ H_2O.$$

In addition, a residual amount of the ammonia can remain unburnt.

In the case of partial conversion of the ammonia, the reacted ammonia can be converted completely into nitrogen without significant formation of nitrogen oxides if appropriate reaction conditions are chosen. However, part of the ammonia remains unreacted.

On the other hand, if a higher conversion is set, for example by increasing the catalyst temperature, nitrogen oxides are generally formed as by-product, so that the offgas comprises not only nitrogen but also quantities of ammonia and nitrogen oxides.

The offgas of the ammonia combustion is then preferably fed to a catalytic reduction plant in which ammonia and nitrogen oxides are converted into nitrogen, for example according to reaction (i3).

Since the $NO_x$ content increases with the ammonia conversion set, the residual amount of ammonia which is not reacted in the ammonia combustion plant should as far as possible correspond stoichiometrically to the amount of $NO_x$, for example be not more than 15%, based on the ammonia content in the offgas fed in.

Since the nitrogen oxides can subsequently be reduced to nitrogen in a catalytic reduction plant, the residual amount of ammonia which remains unburnt should correspond in mole percent according to equation (i3) to not more than the amount of nitrogen oxides formed.

The offgas comprising a small residual amount of ammonia together with nitrogen oxides which is obtained from the regenerative ammonia combustion plant is subsequently fed to an SCR (selective catalytic nitrogen oxide reduction) plant.

While the temperature in the combustion chamber of the ammonia combustion plant for the combustion of ammonia is from 700° C. to 1000° C., preferably from 800° C. to 900° C., the temperature of the catalyst in the catalytic reduction plant is preferably in the range from 180° C. to 500° C., in particular from 200° C. to 380° C. In the SCR plant, it is possible to use commercial DENOX honeycomb catalysts, preferably ones based on titanium dioxide since these are largely insensitive to catalyst poisons and sulfur compounds. Typical residence times are 0.2-0.3 second.

Should the stoichiometry of ammonia to nitrogen oxides not be sufficient, a small sub-stream of the crude offgas which still comprises a large amount of ammonia from the SCR plant is introduced directly in a regulated fashion.

The temperature of, for example, from 800° C. to 900° C. required for reaction of the ammonia in the combustion chamber of the ammonia combustion plant can, if appropriate, be generated solely by the combustion of the ammonia. In the case of concentrations above 3 g/m³, excess energy is present and can be used for heating the prepurified gas in the SCR plant.

However, this liberated energy is preferably introduced into the process for preparing isocyanates, for example to generate steam for the vaporizers of distillations or particularly preferably for the dissociation (f).

However, if the ammonia concentration is low, the combustion chamber temperature is maintained at the desired operating temperature by means of a burner or comparable heating.

For this purpose, additional heating material can be introduced from the outside, for example natural gas, petroleum or naphtha and/or preferably waste streams from the process for preparing isocyanates.

Part, for example from 5 to 25% by volume, of the hot combustion chamber air can be branched off from the combustion chamber and used directly for heating the catalyst of the SCR plant.

The offgas which leaves the ammonia combustion plant at a temperature of, for example, from 40° C. to 10° C. is heated further by passing it through a heat exchanger which is heated by the purified gas leaving the SCR plant.

To balance the heat exchanger loss, the hot combustion chamber air is introduced into the prepurified offgas leaving the heat exchanger.

The addition of the raw, ammonia-rich offgas to the reduction of the $NO_x$ in the offgas prepurified in the regenerative thermal after-combustion plant is set so that the $NO_x$ content of the purified gas leaving the SCR plant is below the permissible limit, which is typically below 500 mg/m³, preferably below 350 mg/m³, particularly preferably below 200 mg/m³, very particularly preferably below 150 mg/m³, in particular below 100 mg/m³, especially below 75 mg/m³ and even below 50 mg/m³ (dry, under standard conditions, calculated as $NO_2$). However, a lower $NO_x$ content significantly below this limit is left in the purified gas if there is otherwise a risk of part of the ammonia fed to the SCR plant breaking through. It should here be taken into account that in general no ammonia should escape into the environment. In general, it is possible to set the con-tent of ammonia in the offgas to not more than 5 ppm, preferably not more than 4 ppm, particularly preferably not more than 3 ppm, very particularly preferably not more than 2 ppm and in particular not more than 1 ppm.

Accordingly, the addition of the raw, ammonia-rich offgas to the prepurified offgas from the ammonia combustion plant is regulated according to the $NO_x$ concentration in the purified gas leaving the SCR plant. For this purpose, the purified gas line from the SCR plant is provided with an $NO_x$ measuring instrument which controls a valve provided in the bypass line connecting the raw gas line to the line for the prepurified offgas leaving the regenerative thermal after-combustion plant.

In the case of a low concentration of, for example, less than 1 g/m³, traces of ammonia remaining in the offgas can be removed by means of an acid scrub.

The ammonia can also be burnt together with organic material. This can be, for example, natural gas, petroleum or naphtha and/or, preferably, waste streams and/or by-product streams from the process for preparing the isocyanates. The ammonia which has been separated off from the process for preparing the isocyanates and fed to the combustion can, as indicated above, comprise a proportion of alcohol which has been separated off and other by-products of the process which can likewise be burnt at the same time. However, the joint combustion with organic material can lead to increased $NO_x$ values.

A high formation of $NO_x$ can be countered to a considerable extent by lowering the flame peak temperatures, reducing the amount of available oxygen in the reaction zone, uniform and rapid mixing of the reactants in the flame, reducing the residence time at high temperatures and reduction of nitrogen oxides already formed at the end of the flame. Numerous apparatuses and processes, for example internal and external flue gas recirculation or addition of water and water vapor, have been developed for this purpose. Internal and external flue gas recirculation involves a process in which the flue gas is cooled either in a sufficiently large combustion chamber or by discharge from the combustion chamber and is reintroduced at a suitable point for lowering the flame peak temperature. Internal recirculation, which involves intensive mixing of the flame gases with relatively cold furnace gases, is of particular importance.

Two-stage combustion with stepped addition of air is likewise of importance for reducing the proportion of $NO_x$ in the offgas and is also effective in the case of nitrogen-containing fuels. Here, the amount of combustion air made available to the fuel in the first combustion stage is such that there is not an excess of oxygen, so that the nitrogen-comprising component comprised in the fuel is broken down to molecular nitrogen as a result of the largely reducing conditions. In the second combustion stage, combustion by means of an excess of oxygen then takes place, but only thermal $NO_x$ formation, which plays a smaller role than formation of $NO_x$ from nitrogen-comprising components comprised in the fuel, now occurs.

A similar solution also forms the basis of three-stage combustion, in which a nitrogen-comprising fuel is firstly reacted in a targeted manner by combustion with an excess of oxygen to form $NO_x$, while in a second combustion stage the $NO_x$ formed is largely reduced again to molecular nitrogen under reducing conditions resulting from an excess of organic material and deficiency of oxygen. In the subsequent third combustion stage, only thermal $NO_x$ formation, which plays a subordinate role in total $NO_x$ formation, once again takes place.

In a reverse of the generally known formation equation for ammonia from the components nitrogen and hydrogen, which usually proceeds at high pressures and high temperatures, ammonia can be at least partly decomposed again into its starting components nitrogen and hydrogen according to equation (i4) at low to standard pressure and elevated temperatures.

These gases obtained from the dissociation can then preferably be thermally utilized in a subsequent combustion.

This reverse reaction proceeds particularly advantageously and virtually quantitatively in the presence of catalysts, in particular in the presence of metals or metal oxides. The decomposition of the ammonia-comprising gas stream therefore advantageously proceeds, in an embodiment of the process of the invention, in the presence of metals or metal oxides as catalysts. In this text, the term "catalyst" is used synonymously both for catalytically active metals and for metal oxides.

If the ammonia-comprising gas stream is dissociated catalytically using catalysts, preferably in a dissociation reactor, the result is, when the necessary stoichiometric ratios are observed, a dissociation gas which comprises essentially only $N_2$, $H_2$ and possibly CO and/or $CO_2$ and/or $H_2O$ when organic components are comprised in the ammonia-comprising gas stream. Such a gas mixture is thus largely free of ammonia and $NO_x$ and can subsequently be burnt by known methods to avoid thermal and prompt formation of $NO_x$. As a result of the energy liberated in this combustion, in particular from combustion of the hydrogen, the energy required for dissociation of the ammonia can be balanced, so that the process can be made energy-efficient.

The catalytic dissociation of the ammonia-comprising gas component is preferably carried out using a catalyst comprising metal and/or metal oxide. When metals are used as catalysts for the dissociation of the ammonia-comprising gas stream, it is advantageous for at least the metal used for the catalytic dissociation to comprise transition elements such as chromium, titanium, niobium, molybdenum, nickel, vanadium or iron, for example in the form of a mixture or alloy.

The individual metals can also be used in pure form if appropriate.

The use of stainless steel as catalyst has been found to be particularly advantageous and is therefore preferred; the elements mentioned are incorporated into the stainless steel in varying compositions and different amounts.

Possible stainless steels here are, in particular, those described, for example in DIN 17440 or DIN 17441. The stainless steel denoted as X6CrNiTi 18 10 according to DIN 17440 is particularly useful. It is here generally sufficient for the dissociation reactor itself or at least its interior surface which comes into contact with the ammonia or the ammonia-comprising gas mixture to consist of the catalytically active catalyst metal or comprise at least a proportion of this. The surface area can be increased if required, for example by milling or roughening or by use in the form of shaped bodies, for example rings, small tubes, turnings, gauzes, screens, wires, woven meshes, braids and packings, by means of which the catalytically active surface area is increased. The catalyst itself may be able to be made more compact in this way.

The use of metal oxides is likewise preferred and, in terms of the effectiveness in the catalytic dissociation of ammonia-comprising gas components, may be regarded as of equal value. The oxides of the abovementioned metals are in principle suitable for this purpose, with the use of nickel oxide as catalyst being particularly preferred. When metal oxide is used as catalyst, the catalyst is generally present in powder form in a catalyst bed in the dissociation reactor, but a fluidized bed is also conceivable. Other catalyst geometries, for example in the form of honeycomb bodies or the like, can likewise be used.

In practice, $NO_x$, HCN and $NH_3$ can be formed in the pyrolysis, i.e. thermal decomposition, of nitrogen-comprising organic compounds or as a result of introduction of organic material into ammonia-comprising streams. The combustion of such gas streams having a content of these substances then leads to significant $NO_x$ contents in the combustion offgases. The proportions of $NO_x$, HCN and $NH_3$ in the combustion offgas therefore have to be suppressed with a high engineering outlay during the combustion process (primary measures) or subsequently have to be removed from the offgas (secondary measures).

The dissociation of the ammonia-comprising gas stream advantageously takes place in a tubular reactor which is charged with catalyst material or comprises catalyst metal or consists of catalyst metal and has a circular, oval, rectangular or square cross section, with other shapes such as configuration as a star or polygon also possibly being useful. The tubular reactor will hereafter also be referred to as "dissociation reactor".

To heat the dissociation reactor, it is possible to use an external energy source, but it is particularly advantageous for the desired catalyst temperature to be at least largely maintained by the energy obtainable from the firing power of the burner (see below). This is particularly preferably achieved by using the residues from the process for pre-paring isocyanates, and among these particularly preferably the streams $(e_H)$, $(f_H)$ and/or $(g_H)$.

The dissociation gas formed in the dissociation and intended for combustion advantageously comprises only the components $N_2$, $H_2$ and possibly CO, $CO_2$ and $H_2O$ since an optimal combustion low in $NO_x$ emissions is ensured in this way. Soot formation (in the case of a deficiency of oxygen) or high $NO_x$ formation (in the case of an excess of oxygen) may occur and sensitively interfere in the dissociation process. The presence of water which may be formed in the dissociation in the dissociation gas stream does not have an adverse effect on the combustion. The catalysts used in the dissociation display a particularly high effectiveness when they are brought to an elevated temperature. Satisfactory results can be achieved in a temperature range from about 200° C. to about 1200° C., and it is particularly advantageous for the catalyst to reach a working temperature of from about 500° C. to about 1000° C., preferably from about 650° C. to 1000° C.

To heat the dissociation reactor, it is possible to use an external energy source, but it is particularly advantageous for the desired catalyst temperature to be set and/or maintained at least largely, preferably completely, by means of the energy obtainable from the firing power of the burner.

In the case of particular mixtures of constituents in the pyrolysis gas, it is possible for a strongly exothermic reaction which increases the catalyst temperature above the temperature range required for ideal reaction conditions to occur under some circumstances (for example in the presence of large amounts of $NO_x$ in the simultaneous presence of $H_2$). In this case, water can be introduced to cool the reaction mixture or the dissociation reactor can be externally cooled by introduction of water into the combustion chamber or by means of heat exchangers along the dissociation reactor.

It is appropriate but not absolutely necessary for the gas fed into the dissociation reactor to be exclusively or predominantly ammonia. It is likewise possible for the ammonia to be present in admixture with a gas stream originating from another source which is to be utilized, for example, as carrier gas. The proportion of ammonia in the gas fed to the dissociation can therefore vary within wide limits for the purposes of the process. Thus, proportions of ammonia of less than about 1% by weight of the total amount of gas are possible, and the upper limit is 100% by weight. Although the process can be carried out below a proportion of about 1% by weight, for example at about 0.5% by weight or less, it is no longer economically viable.

However, the process can be operated at any ammonia content in the range from about 1% by weight to about 100% by weight. Thus, proportions of, for example, 10% by weight, 20% by weight, 40% by weight, 60% by weight or 80% by weight of ammonia can be dissociated and subsequently burnt in a combustion apparatus with low emissions of $NO_x$.

The combustion can in principle be carried out in one, two or three stages. Internal and external flue gas circulation (see above) can be employed in the combustion, preferably internal flue gas circulation and, in addition or instead, addition of water or water vapor to reduce the flame peak temperatures.

To ensure very low $NO_x$ emissions when employing a single-stage combustion process, the dissociation of the ammonia-comprising gas stream should have proceeded very completely in the dissociation reactor before entering into the combustion chamber, i.e. the dissociation gas should comprise only the components $N_2$, $H_2$ and possibly CO and/or $CO_2$ and/or $H_2O$. The extent to which the pyrolysis gas dissociation should be carried out in the dissociation reactor depends on the ammonia loading of the gas fed in. If the offgas comprises only small amounts of ammonia, a conversion in the dissociation of, for example, 30, 40 or 50% can be sufficient under some circumstances. However, the gas fed in will usually be laden with larger amounts of ammonia. Since it can generally be assumed that at least 80% of the ammonia entering the combustion chamber is converted into nitrogen oxides, generally not more than about 200 ppm, advantageously not more than about 150 ppm and in particular not more than about 100 ppm, of ammonia should be comprised in the dissociation gas. This means that the dissociation yield of the catalyst, for example based on an ammonia concentration of 100% before entering into the dissociation reactor, should be at least 99.98%. The dissociation yield is advantageously at least 99.99% or more. Higher dissociation yields of course result in a further reduction of the $NO_x$ emissions.

At lower concentrations of ammonia, it is of course also possible for a lower $NO_x$ emission value to be achieved even at a lower dissociation performance of the dissociation reactors. Thus, for example, at a concentration of 10% of ammonia before entering into the dissociation reactor, a dissociation performance of 99.9% is sufficient in order, for example, to adhere to a concentration of 100 ppm in the gas to be fed into the combustion chamber. A further reduction in the ammonia content before entering the dissociation reactor to, for example, 1% requires only a 99% dissociation yield of the catalyst. The corresponding performance requirements for other ammonia concentrations can be calculated very easily by a person skilled in the art. "At least substantial" dissociation therefore means a dissociation yield which leaves not more than 300 ppm, preferably less than 250 ppm and in particular 100 ppm or less, of ammonia in the gas flowing out of the dissociation reactor. A further possible way of regulating the dissociation performance of the catalyst is to appropriately choose the residence time of the gas stream to be dissociated in the dissociation reactor.

In general, the residence time should be from about 0.1 to 10 seconds, with residence times of from 0.2 to 5 seconds and in particular from 0.3 to 3 seconds being particularly preferred. In general, very good results can be achieved using residence times in the range from about 0.5 to 2.5 seconds. Parameters which decide the choice of the residence time are, for example: material of the catalyst, geometry of the catalyst, pressure drop over the catalyst, turbulence, etc.

The residence time of the ammonia-comprising gas to be dissociated in the dissociation reactor is also dependent on its temperature. In general, an increasing temperature of the dissociation reactor makes a shorter residence time necessary for at least substantial dissociation. While in the case of a dissociation reactor at from about 700 to 900° C., the residence time of the gas in the dissociation reactor should be from about 0.5 to 5 seconds, the residence time necessary for at least substantial dissociation can be reduced significantly by means of an increase in the temperature. For example, it is thus possible, depending on the effectiveness of the catalyst, to achieve at least substantial dissociation of ammonia in the offgas using residence times of less than 0.5 second, preferably less than 0.4 second and particularly preferably less than 0.3 second, at dissociation reactor temperatures of from 900 to about 1000° C.

The gas streams which can be disposed of by means of the process may comprise, in addition to ammonia, further components which can have an adverse effect on operation of the catalyst.

As a result of the operation of the dissociation reactor under generally reducing conditions, hydrocarbon-comprising impurities or impurities made up at least largely of hydrocarbons can lead to soot formation and thus to deactivation of the catalyst surface. Hydrocarbons such as methane, ethane, propane and also higher, unbranched or branched paraffins, unbranched or branched olefins, in particular, but also alcohols such as methanol, ethanol, propanol or butanol lead to soot formation in the dissociation reactor and therefore to deposits on the catalyst. As a result, due to restriction of the dissociation, the $NO_x$ values can rise above the desired or permissible limit value after only a short time.

Such soot formation can be prevented by introducing a small amount of oxygen which is just sufficient for oxidation of the impurities to form a mixture of predominantly carbon monoxide and hydrogen gas into the gas stream fed in. In general, such an oxidation can be achieved by mixing an amount of oxygen which corresponds to half that necessary for total combustion of the impurities into the gas. The addition of oxygen usually does not result in any increase in the $NO_x$ values in the combustion offgas, but instead values which correspond to those without hydrocarbon-comprising impurities in the offgas can be achieved in this way.

The combustion of the gas obtained from the dissociation (dissociation gas) preferably takes place in combustion apparatuses using impulse burners. Impulse or high-velocity burners have a nozzle outlet for the combustion air which makes up the major part of the mass flow of combustion air. The combustion air flowing out of the inlet nozzle or nozzles at a high exit impulse results in an injector action in the vicinity of the exit nozzles which draws in the combustion offgases from the heating space and mixes them into the combustion air. The occurrence of such an effect is strongly dependent on the exit or flow velocity of the combustion air leaving the nozzles.

The combustion of the dissociation gas formed in this way can advantageously be carried out using impulse burners operating with natural gas, with the dissociation gas being fed in in the backflow region of the flue gases of the impulse burner. This form of introduction results in the dissociation gas being exposed to an increasing $O_2$ concentration profile, which contributes to a lowering of the flame peak temperature.

It is likewise possible to preheat the air used for combustion to an elevated temperature of up to 1000° C. However, particularly good results are obtained when the air temperature is from about 100° C. to about 600° C. and in particular from about 200° C. to about 400° C.

As a general guide, exit velocities of from about 80 to about 120 m/sec are necessary for impulse burners. However, this value can be even higher if the combustion space is appropriately constructed. The process of the invention can in this way be carried out without problems even at exit velocities of more than 130, 140 or 150 m/sec. Exit velocities below 80 m/sec are also generally no obstacle in carrying out the process described here. Thus, an appropriate backflow of gas can also be realized even at exit velocities of less than 80 m/sec, for example 70 or 60 m/sec. Exit velocities of less than 60 m/sec require a special construction of the combustion chamber in order to produce sufficient backflow of offgas.

For the purpose of the present text, impulse burners are burners in which the exit velocity of the combustion air is high enough to ensure a sufficient backflow of offgas. The flow of the hot gases present in the combustion chamber in the direction of the inlet nozzles for the combustion air will hereinafter also be referred to as "backflow". Such impulse burners, which are increasingly being used for the conversion of fuel energy into heat, are generally operated as single-stage burners.

According to the invention, the dissociation reactors for dissociation of the pyrolysis gas are preferably heatable. It is particularly advantageous for the dissociation reactor to be able to be heated by the energy arising from the firing power of the burner. In a particular embodiment, this is achieved by at least part of the length of the dissociation reactor projecting into the interior of the combustion chamber.

The multistage process of the invention for the continuous preparation of organic iso-cyanates with recirculation and discharge of the by-products makes it possible to pre-pare distillable isocyanates, preferably diisocyanate, with high selectivity in very good yields.

The process of the invention is particularly useful for preparing aliphatic diisocyanates such as 2-methylpentane, 1,5-diisocyanate, isomeric aliphatic diisocyanates having 6 carbon atoms in the alkylene radical and mixtures thereof and preferably hexamethylene 1,6-diisocyanate and cycloaliphatic diisocyanates, in particular 3-isocyanatomethyl-3,5,5-trimethylcyclohexyl isocyanate 4,4'-di(aminocyclohexyl)methane by an economical method.

The isocyanates prepared are very well suited to the preparation of polymers comprising urethane, isocyanurate, amide and/or urea groups by the polyisocyanate-polyaddition process. They are also used for preparing polyisocyanate mixtures modified with urethane, biuret and/or isocyanurate groups. Such polyisocyanate mixtures derived from aliphatic or cycloaliphatic diisocyanates are used, in particular, for producing light-resistant polyurethane paints and coatings.

In a preferred embodiment, the overhead fraction obtained in the purification of the crude isocyanate (f) by distillation is recirculated to reaction step (a), the side fraction, which consists of essentially pure isocyanate, is conveyed to a container for storage and the bottom fraction is recirculated to reaction step (a) or (d) or (a) and (d).

The following examples illustrate the invention but do not restrict it to these examples.

EXAMPLES

Example 1

1.01 kg/h of 1,6-hexamethylenediamine (HDA) and 1.2 kg/h of liquid urea were metered continuously into a continuously operated apparatus comprising a 20 liter pressure autoclave with heating jacket, a rectification column mounted on the reactor and a condensation system. The about 4.3 kg/h of n-butanol necessary for the reaction, which at the same time functions as solvent, were metered in at the top of the column in addition to the runback of 6.3 kg/h necessary for the separation column. The pressure in the reactor was 10.5 bar. The temperature was set to 220° C. by means of the heating medium. About 4.8 kg/h of a reaction mixture whose main constituents are 39% by mass of n-butanol and about 43% by mass of dibutylurethane left the reactor.

Ammonia was formed during the reaction of the HDA. This left the reactor together with n-butanol (boiling temperature) and was largely separated off from the butanol in the rectification column. The vapor stream from the column, which had a temperature of about 192° C., was mostly condensed at 160° C. in a glass condenser (water cooling). At the settings in the experiment, the amount of condensate was 6.3 kg/h. The gas stream of about 150 l/h leaving the condenser, comprised, according to analyses, about 65% by mass of n-butanol and 34.6% by mass of ammonia and was well suited to combustion.

Example 2

The apparatus as described in Example 1 is operated using the same metered-in amounts of diamine, urea and n-butanol, with the difference that the column has been removed and the gas stream from the reactor is condensed directly in the condenser. The n-butanol feed stream of 4.2 kg/h is instead metered directly into the reactor. The condensation temperature in the condenser is maintained at 160° C. by means of the cooling medium. The pressure in the apparatus is set to 10.5 bar by means of a pressure regulator. The mean residence time of the liquid in the reactor, the thermal power introduced by means of Marlotherm fluid, the output of about 4.8 kg/h and the n-butanol and dibutylurethane concentrations are about the same as those in Example 1.

The omission of the column enables the reactor temperature to be reduced to only 212-214° C., with the result that a smaller content of by-products occurs in the product and the apparatus requires less regulation because of the omission of the column. The composition and amount of the ammonia gas stream are approximately comparable to those in Example 1.

The invention claimed is:

1. A process for preparing an isocyanate comprising reaction of an amine with urea and at least one alcohol to form the corresponding urethane with liberation of ammonia, followed by dissociation of the urethane into the corresponding isocyanate, wherein the ammonia liberated is at least partly utilized thermally by utilizing heat liberated by an exothermic reaction of the ammonia, wherein the energy liberated in the thermal utilization is at least partly utilized for the dissociation of the urethane.

2. The process according to claim 1, wherein the thermal utilization of the ammonia comprises a conversion into molecular nitrogen ($N_2$).

3. The process according to claim 1, wherein the thermal utilization of the ammonia comprises a conversion into nitrogmonoxide (NO).

4. The process according to claim 1, wherein the utilization of the ammonia comprises a conversion into urea or melamine.

5. The process according to claim 2, wherein offgases from the process comprise less than 350 mg/m$^3$ of nitrogen oxides ($NO_x$).

6. The process according to claim 1, wherein residues from the process are fed together with ammonia to the thermal utilization.

7. The process according to claim 5, wherein residues from the process are fed together with ammonia to the thermal utilization.

* * * * *